United States Patent [19]

Brezinski

[11] 4,360,415

[45] Nov. 23, 1982

[54] NOISE SUPPRESSING BYPASS FOR REFERENCE ELECTRODE

[75] Inventor: Donald P. Brezinski, Corning, N.Y.

[73] Assignee: Corning Glass Works, Corning, N.Y.

[21] Appl. No.: 230,457

[22] Filed: Feb. 2, 1981

[51] Int. Cl.³ .......................................... G01N 27/30
[52] U.S. Cl. ................................................ 204/195 F
[58] Field of Search ................ 204/1 T, 195 F, 195 R

[56] References Cited

U.S. PATENT DOCUMENTS

| 3,103,480 | 9/1963 | Watanabe et al. | 204/195 G |
| 3,486,998 | 12/1969 | Sellers et al. | 204/195 T |
| 3,676,319 | 7/1972 | Kirsten | 204/195 F |

OTHER PUBLICATIONS

"Ion-Selective Electrodes", NBS Special Publication 314, Nov., 1969, pp. 430-432.
"Experimental Electrochemistry for Chemists", 1974, pp. 286-288.

*Primary Examiner*—T. Tung
*Attorney, Agent, or Firm*—William E. Maycock; Clinton S. Janes, Jr.

[57] ABSTRACT

Spurious a.c. noise signals impressed upon an electrochemical reference electrode 3 with separate half-cell and junction electrolytes are reduced by a low impedance bypass circuit including a capacitor 25 connected in series between the electrode lead wire 15 and an inert electronic conductor, such as a graphite rod 27, immersed in the junction electrolyte solution.

5 Claims, 4 Drawing Figures

NOISE SUPPRESSING BYPASS FOR REFERENCE ELECTRODE

BACKGROUND OF THE INVENTION

The present invention is concerned with reference electrodes which are employed to provide the stable reference potentials required by a variety of electroanalytical techniques, such as ion selective electrode measurements, controlled potential coulometry, polarography, and the like.

A reference electrode most frequently is used in conjunction with an ion-selective electrode to measure the activity (which is a function of concentration) of a given ion in a sample solution. Consequently, the discussion which follows primarily relates to such use. It is to be understood, however, that such discussion is not intended to in any way limit the spirit or scope of the present invention.

The two electrodes, i.e., the reference electrode and the ion-selective electrode, both of which are immersed in the sample solution, typically are connected to a means for measuring the potential difference between the electrodes, e.g., an electrometer. The reference electrode provides a constant electromotive force or potential against which the potential of the ion-selective electrode is compared. The latter potential consists of a constant component from the electrochemical half-cell of the ion-selective electrode and a variable component which is the potential across the sensing membrane and which is dependent upon the activity (concentration) of the ion being measured. The variable component, then, is readily correlated with ion activity (concentration) by known means. To give accurate results, the potential of the reference electrode should not change with the composition of the sample.

The reference electrode is designed to be minimally sensitive to changes in the external, sample ionic environment. It consists of at least three components: (1) a half-cell electrode (typically a silver-silver chloride mixture), (2) a half-cell electrolyte (typically 4 M potassium chloride solution saturated with silver ions), and (3) a reference junction. The half-cell electrode and half-cell electrolyte constitute an electrochemical half-cell having a known, stable, constant electrical potential. Direct physical, and therefore electrical, contact between the half-cell electrolyte and the sample solution is established through the reference junction which usually consists of a porous ceramic plug, metal or asbestos fiber bundle, sintered plastic, or like means of achieving a fluid mechanical leak.

As used herein, the term "half-cell electrode" means the solid-phase, electron-conducting contact with the half-cell electrolyte, at which contact the half-cell oxidation-reduction reaction occurs which establishes the stable potential between the half-cell electrolyte and the contact.

In more sophisticated reference electrode designs, separate electrolytes are used for the half-cell and reference junction and these electrolytes are separated by a barrier through which ionic conduction may occur. For example, double-junction reference electrodes utilize an inner junction of porous ceramic or other material to separate dissimilar outer junction and half-cell electrolytes. Likewise, the diffusion barrier and ion-selective barrier reference electrodes, described in applicant's copending applications 233,993 Ser. Nos. and 233,996, respectively filed Feb. 12, 1981, use low-permeability barriers having either low electrolytic conductivity or high ionic specificity respectively, to prevent flow or diffusion of heavy metal ions from the half-cell electrolyte into a similar junction electrolyte (usually pure 4 M KCl) which is free of heavy metal ions. In these cases, the inner junction, diffusion barrier, or ion-selective barrier adds to the resistance of the electrode, which makes measurements using the electrode more susceptible to electrical noise.

Such electrical noise arises from extraneous, fluctuating electric and magnetic fields, or from proximate voltage and current sources, that are coupled to the measurement circuit and tend to induce spurious changes in the potential between the ion and reference electrode termini of the electrometer. Reference electrodes typically have impedances ranging from $1-20K\Omega$, whereas ion-selective and glass pH electrodes typically have impedances ranging from $100K\Omega$ to over $1000M\Omega$. Other things being equal, the latter electrodes would be expected to contribute more noise to the measurement. However, particular care is usually taken to shield the entire cable leading from the active surface of the ion sensor to the high impedance input of the electrometer. This shielding is particularly good in combination electrodes where the internal components and lead wire of the ion sensor are completely surrounded by the electrolyte of the reference portion of the electrode and by the braided shield of the electrode cable, which also serves as the reference lead. Thus, the pH "internals" and cable are almost always well protected from stray electric and magnetic fields. On the other hand, the reference lead is almost invariably exposed to the electrical environment, whereby stray electric or magnetic fields may more readily induce current flow along it. More importantly, the sample in which the electrodes are immersed is often the source of stray currents which tend to pass via the reference electrode into the negative input of the electrometer. Typically, the negative input is connected to circuit ground and has a relatively low impedance, and therefore acts as a "sink" for stray a.c. currents. In contrast, the positive input of the electrometer has relatively high impedance, and admits negligible current. Stray fluctuating currents can be injected by, for example, the random or periodic cycling of nearby electrical machinery, thermal controllers in water baths, hand waving, the insertion of charged bodies into the sample being measured, etc. Currents passing through the reference electrode impress a voltage in proportion to its impedance, thus causing the potential of the solution to change relative to the reference (negative) terminal of the electrometer. The potential of the pH or ion electrode, which is well shielded and connected to the high impedance positive input terminal of the electrometer, will simply follow the change in potential of the solution. The result is an a.c. noise component in the measurement, which is impressed primarily across the reference impedance. Since the coupling impedance of noise sources is usually quite high, the noise impressed across the reference electrode is directly proportional to its impedance.

One approach to a specialized problem of noise is disclosed in published British patent application No. 2,027,897, wherein a wire conductor extends through the central glass conduit of an ionic test cell through which an air bubble segmented test solution flows. The conductor provides a low impedance shunt path through the solution to reduce signal distortion due to circuit impedance fluctuations arising from interruptions of the solution path between the ionic and reference sensors by air bubbles. This addresses a completely different noise source problem than that developed above, however, and would not be effective in eliminating noise due to the reference electrode impedance, and would be inapplicable to a reference electrode environment due to, inter alia, the different redox potentials of the half-cell, junction electrolyte, and test solutions.

SUMMARY OF THE INVENTION

Most electrical noise, especially impulse noise, is comprised primarily of high frequency components, so it is the a.c. rather than the d.c. impedance of the electrode which is critical. The d.c. impedance of electrolyte barriers serves to retard the cross-diffusion of the electrolytes, but the a.c. impedance serves no useful purpose and causes increased susceptibility to electrical noise.

Accordingly, in the present invention the a.c. impedance of a diffusion barrier, ion-exchange barrier, or double junction reference electrode is lowered by means of capacitative coupling between the half-cell and junction electrolytes to thus bypass or suppress a.c. noise components and prevent them from contaminating the measurement signal. The bypass circuit may simply comprise a miniature capacitor connected in series between the half-cell contact and an inert conductor, such as a platinum wire or carbon rod, immersed in the junction electrolyte. Since the impedance of the capacitor is inversely proportional to frequency, high frequency a.c. noise components are bypassed directly around the high resistance barrier.

DETAILED DESCRIPTION OF THE PREFERRED EMBODIMENT

Figure 1:
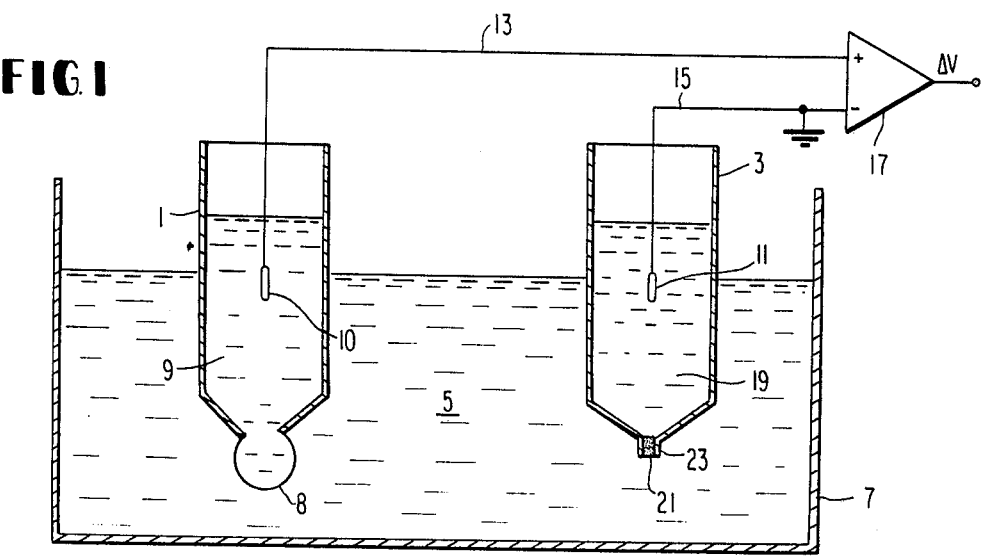
FIG. 1 shows a simplified schematic diagram of a typical pH measurement system, illustrating the essential components thereof.

FIG. 1 illustrates the essential elements of a typical pH measurement system. A pH electrode 1 and a reference electrode 3 are partially immersed in a sample solution 5 in a container 7, and both electrodes are electrically connected to electrometer 17 by conductors 13 and 15. The potential across the glass sensing membrane 8 of the pH electrode changes in proportion to the difference in pH between the external sample solution 5 and a pH buffer solution 9 contained within the sensor membrane. An electrochemical half-cell 10 is used to establish a stable electrical connection between an buffer solution 9 and the wire conductor 13 leading to the electrometer. This half-cell has a fixed potential determined by the chloride ion concentration of the buffer solution. The difference in potential between the external sample solution 5 and the positive electrometer terminal changes with pH, and it is this change in potential that is to be monitored. The role of the reference electrode is to establish a fixed half-cell potential between the external solution being measured and the negative electrometer terminal. In measurements of unknown solutions, the half-cell cannot be directly immersed in the sample since its potential will vary with the unknown anionic, e.g., chloride ion, activity of the solution. Therefore, an indirect connection is made by immersing the reference half-cell 11 into a known electrolyte 19 (usually AgCl-saturated 4 M KCl), and then establishing physical and electrical contact between this electrolyte and the measured solution through a reference junction 21 positioned in the outlet 23 of the electrode envelope. The reference junction usually consists of a porous ceramic plug, asbestos fiber, or other means of achieving a fluid mechanical leak. The reference junction functions primarily as a flow restrictor and filtration member, and also serves to define the shape of the interface between the solutions. Ideally, the junction is sufficiently porous to allow a low resistance contact, preferably well below 10K$\Omega$, between the external and internal solutions, but is not so porous that the solutions become mutually contaminated.

Figure 2:
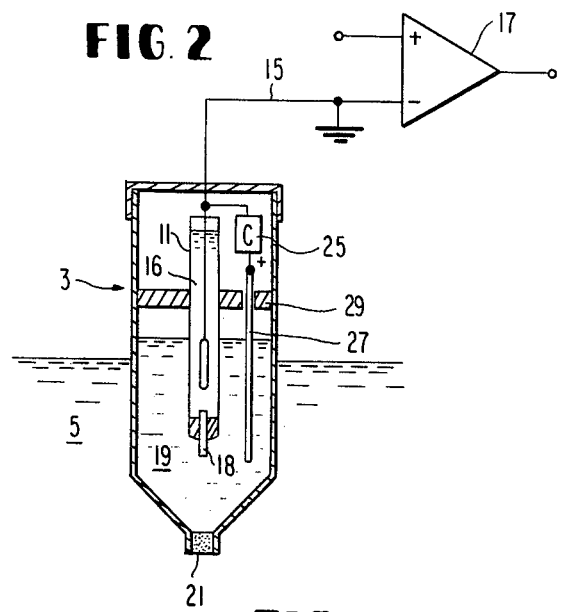
FIG. 2 shows a more detailed elevation view, partly in section and having a distorted scale for clarity, of a diffusion barrier type of reference electrode provided with a noise suppressing bypass circuit according to the present invention.

In a double junction, diffusion barrier, or ion-selective barrier reference electrode, the reference half-cell 11 and electrolyte 19 of FIG. 1 would be separated by an electrolytically conductive barrier which further increases the electrical impedance between the sample 5 and reference conductor 15. Such a barrier is shown in FIG. 2, which also illustrates the present invention. Half-cell electrolyte 16 and junction electrolyte 19 are separated by a porous barrier 18 which retards mixing of these electrolytes but also increases the impedance of the reference electrode. The noise suppressing bypass circuit according to the present invention will be seen to comprise a capacitor 25 connected in series between the wire conductor or lead 15 or the reference electrode and an inert electrically conducting rod member 27 immersed in the junction electrolyte 19. Both the rod member 27 and the half-cell 11 envelope are mounted in and extend through apertures in a dielectric bushing 29 disposed within the electrtode envelope above the liquid level. The capacitor 25 may be a miniature tantalum electrolytic capacitor such as the Minitan SR-06-476-°manufactured by Corning and having a capacitance of approximately 50 $\mu$f at 6 volts, but lower quality components would equally suffice.

For the rod member 27 a number of materials are acceptable. The coupling between the rod member and the 4 M KCl solution is primarily capacitive. The solution/rod member electrical interface is very thin and can provide a differential capacitance exceeding several hundred $\mu$f/cm$^2$. A number of electronic conductors including carbon, platinum, and tin oxide were evaluated for suitability as the rod member or bypass contact. The main performance requirements are the absence of corrosion and an interfacial capacitance significantly exceeding that of the coupling capacitance ($\sim$50 $\mu$f). The interfacial capacitances of these conductors were determined by immersing them in 4 M KCl solution, applying a constant current pulse of 1 $\mu$A for approximately one minute, and measuring the resulting shifts in conductor/solution potential. The best rod member from all standpoints (cost, convenience and performance) was found to be a simple mechanical drawing pencil lead (graphite) such as the Mars Lumograph H or the A. W. Faber 1930. The measured differential capacitance of these graphite-containing rods was $\sim 3000$ $\mu f$, which was nearly that of a platinized platinum wire.

The potentials of the immersed platinized platinum and graphite lead conductors were fairly similar, about 200–300 mV positive with respect to the Ag/AgCl half-cell. The potential stayed in this range with a variety of electrolytes, including 4 M KCl, 0.01 M KCl and 4 $M_4NH_3$. This potential is probably established by the half-cell reaction $O_2 + 2H^+ + 2e^- \longleftrightarrow H_2O_2$, which has a calculated potential of about $+230$ mV relative to Ag/AgCl at pH 7 and with $1/2O_2 + H_2O \longleftrightarrow H_2O_2$ at equilibrium.

When the bypass capacitor 25 is connected with the polarity shown in FIG. 2 its dielectric is preserved by the difference in potential between the two half-cells. Even though the test capacitor used was rated at 6 V breakdown, the external junction of the reference electrode limits the breakdown current to 10 $\Omega$/volt up to applied voltages of 100 V. The overall reference electrode configuration tested survived the direct application of $+100$ V and 25 V, which thus provides reasonable protection against voltage surges. The capacitor 25 itself survived 100 V of reverse bias for several minutes, but punched through at 30 V forward bias.

All of the required components for the noise suppressing bypass circuit of the invention fit within the outer envelope of a Corning Model 476029 reference electrode, and were potted in place with epoxy prior to testing.

Figure 3:
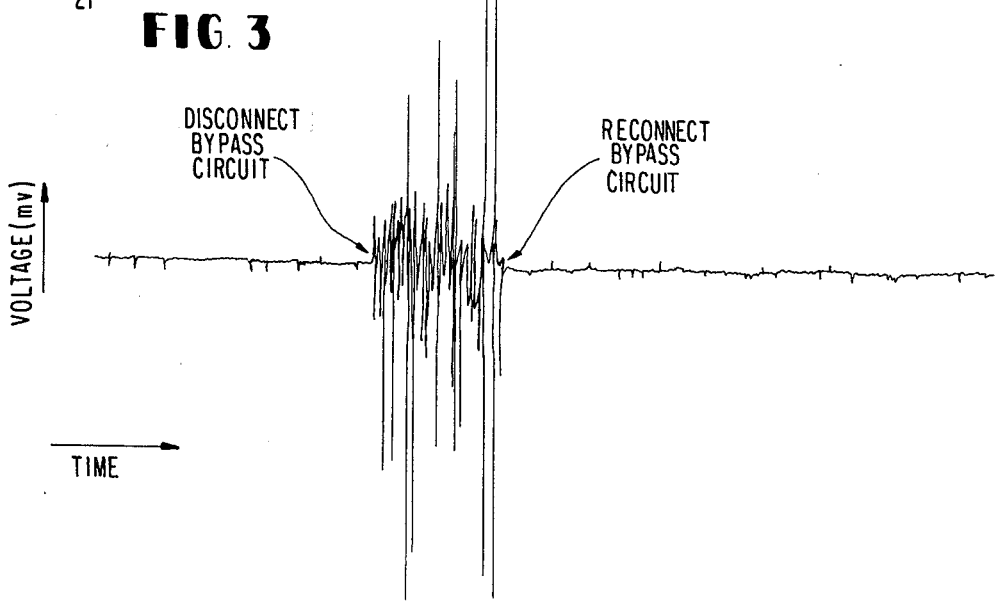
FIG. 3 shows a replica of an actual strip chart recording of an ion meter output equipped with the present invention and illustrating the noise suppressing effect thereof.

The effectiveness of the bypass circuit in suppressing a.c. noise components is graphically illustrated in FIG. 3, for which a strip chart recorder was used to follow the drift of electrodes immersed in a hot water bath. The cycling of the thermal controller for the bath caused large spikes on the recorder output, but these were markedly reduced when the bypass circuit was connected to the electrode as shown in FIG. 2. In conducting this particular test the resistance of the reference junction 21 was minimized to clearly demonstrate that the attenuation was nearly complete over the entire frequency domain of the noise signals.

Figure 4:
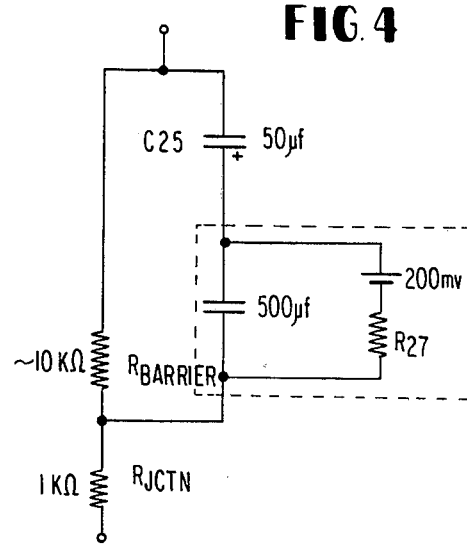
FIG. 4 shows a schematic diagram of an equivalent circuit of a reference electrode provided with a noise suppressing bypass according to the invention.

The equivalent circuit of the noise suppressed reference electrode is schematically shown in FIG. 4. The portion of the circuit enclosed by the broken line represents the electrical behavior of the conductor/solution interface. The a.c. impedance of the conductor/solution interface is negligible compared to that of the coupling capacitor 25, whereby the a.c. impedance of the electrode is simply $R_J + R_B/(1 + j\omega R_B C)$, where $\omega$ is the angular frequency. The overall impedance may thus be approximated at $R_J + R_B$ at very low frequencies, and at $R_J$ for high frequencies, whereby the a.c. noise components are effectively suppressed by a factor of $R_J/(R_B + R_J)$.

The smoothing time constant of the bypass circuit is given by the product of the barrier resistance and the coupling capacitance, or roughly $10K\Omega \times 50$ $\mu f \simeq 0.5$ seconds. shorter period than this will be suppressed. In contrast to analog or digital smoothing within the electrometer, which slows down response, the capacitative bypass has no effect on response time to changes in the external sample solution. Changes in electrode potential arise from diffusion potentials at the external reference junction. A change in the junction potential causes little, if any, current flow through the reference electrode; thus, the charge on the bypass capacitor 25 is not disturbed.

Variations of the present invention will be apparent to the skilled artisan. The essence of the present invention is the suppression of electrical noise of a reference electrode means with separate half-cell and junction electrolytes by means of capacitative coupling between electronic conductors immersed in these electrolytes, and this invention can be employed in configurations other than those specifically shown. For example, noise in blood gas and electrolyte measuring instrumentation can be reduced by connecting capacitors between the reference half-cell of the instrument and one or more electrically conductive fittings (e.g., stainless steel) through which electrolyte solutions are routed.

What is claimed is:

1. In a reference electrode comprising a housing containing an electrochemical half-cell including a half-cell electrolyte, a junction electrolyte and a reference junction allowing ionic conduction between said junction electrolyte and an external sample, and an internal junction or barrier allowing ionic conduction between said half-cell electrolyte and said junction electrolyte, the electrochemical half-cell being electrically connectable to an external measuring means, the improvement characterized by:
a capacitor means electrically connected between said half-cell and an electronic conductor at least partially immersed in said junction electrolyte, whereby high frequency a.c. noise signals are suppressively bypassed around said internal junction or barrier and through the low a.c. impedance path presented by said capacitor and said electronic conductor.

2. A reference electrode as defined in claim 1, wherein the capacitor is an electrolytic capacitor.

3. A reference electrode as defined in claim 2, wherein the electronic conductor has an interfacial capacitance with the junction electrolyte at least as great as the capacitance of the capacitor.

4. A reference electrode as defined in claim 3, wherein the electronic conductor is a conductive form of carbon, such as graphite.

5. A reference electrode as defined in claim 4, wherein the electronic conductor has the form of an elongated rod.

* * * * *